US012690755B2

(12) United States Patent
Yi et al.

(10) Patent No.: US 12,690,755 B2
(45) Date of Patent: Jul. 28, 2026

(54) ENDOSCOPIC BENDING SECTION AND ENDOSCOPE

(71) Applicant: GUANGZHOU RED PINE MEDICAL INSTRUMENT CO., LTD., Guangzhou (CN)

(72) Inventors: Feng Yi, Guangzhou (CN); Jing Li, Guangzhou (CN); Xiaofeng Tan, Guangzhou (CN)

(73) Assignee: GUANGZHOU RED PINE MEDICAL INSTRUMENT CO., LTD., Guangzhou (CN)

( * ) Notice: Subject to any disclaimer, the term of this patent is extended or adjusted under 35 U.S.C. 154(b) by 249 days.

(21) Appl. No.: 18/575,069

(22) PCT Filed: Dec. 5, 2022

(86) PCT No.: PCT/CN2022/136476
§ 371 (c)(1),
(2) Date: Dec. 28, 2023

(87) PCT Pub. No.: WO2023/103937
PCT Pub. Date: Jun. 15, 2023

(65) Prior Publication Data
US 2024/0293013 A1 Sep. 5, 2024

(30) Foreign Application Priority Data
Dec. 7, 2021 (CN) .......................... 202111485757.0

(51) Int. Cl.
 *A61B 1/005* (2006.01)
 *A61B 1/00* (2006.01)
(52) U.S. Cl.
 CPC .......... *A61B 1/0057* (2013.01); *A61B 1/0055* (2013.01)

(58) Field of Classification Search
CPC . A61B 1/0057; A61B 1/0055; A61B 1/00064; A61B 1/0051; A61B 1/01
See application file for complete search history.

(56) References Cited

U.S. PATENT DOCUMENTS

| | | | |
|---|---|---|---|
| D277,406 S | 1/1985 | Imada | |
| D277,407 S | 1/1985 | Imada | |

(Continued)

FOREIGN PATENT DOCUMENTS

| | | |
|---|---|---|
| CN | 105911687 A | 8/2016 |
| CN | 206007203 U | 3/2017 |

(Continued)

OTHER PUBLICATIONS

Chinese Office Action (w/ English translation) for corresponding Application No. 202111485757.0, dated Mar. 27, 2024, 13 pages.

(Continued)

*Primary Examiner* — Anh Tuan T Nguyen
*Assistant Examiner* — Rynae E Boler
(74) *Attorney, Agent, or Firm* — Dority & Manning, PA

(57) ABSTRACT

Disclosed are an endoscopic bending section and an endoscope. The endoscopic bending section comprises a wire winding portion, the wire winding portion being provided with a mounting cavity, and a first traction wire hole, a second traction wire hole, a third traction wire hole and a fourth traction wire hole which are arranged around the mounting cavity at intervals, wherein the mounting cavity, the first traction wire hole, the second traction wire hole, the third traction wire hole and the fourth traction wire hole all extend in an axial direction of the wire winding portion; and the wire winding portion is provided with at least three wire-passage holes arranged at intervals in a circumferential (Continued)

direction of the wire winding portion, the wire-passage holes separately being in communication with the mounting cavity.

9 Claims, 4 Drawing Sheets

(56) References Cited

U.S. PATENT DOCUMENTS

| | | | | |
|---|---|---|---|---|
| D484,594 | S | 12/2003 | Hayamizu | |
| D498,846 | S | 11/2004 | Hayamizu et al. | |
| D638,937 | S | 5/2011 | Tanaka | |
| D649,244 | S | 11/2011 | Nohara et al. | |
| D668,762 | S | 10/2012 | Makowski et al. | |
| D669,175 | S | 10/2012 | Makowski et al. | |
| D777,328 | S | 1/2017 | Tanaka et al. | |
| D777,915 | S | 1/2017 | Tanaka et al. | |
| 2017/0266410 | A1* | 9/2017 | Farrell | A61M 1/84 |
| 2019/0167070 | A1 | 6/2019 | Ide | |
| 2019/0175875 | A1* | 6/2019 | Mirzalou | A61M 25/0147 |
| 2020/0113412 | A1* | 4/2020 | Jensen | A61B 1/0055 |
| 2020/0187765 | A1 | 6/2020 | Ide | |
| 2020/0316349 | A1 | 10/2020 | Smith | |
| 2021/0146096 | A1* | 5/2021 | Yamada | A61M 25/0147 |
| 2023/0165444 | A1* | 6/2023 | Schütz | A61B 1/0057 600/149 |
| 2023/0404375 | A1* | 12/2023 | Jensen | A61B 1/0055 |

FOREIGN PATENT DOCUMENTS

| | | | |
|---|---|---|---|
| CN | 111035347 | A | 4/2020 |
| CN | 212521715 | U | 2/2021 |
| CN | 212729740 | U | 3/2021 |
| CN | 113974530 | A | 1/2022 |
| CN | 216702510 | U | 6/2022 |
| JP | 2012040258 | A | 3/2012 |
| JP | 2021087479 | A | 6/2021 |
| KR | 1020160056725 | A | 5/2016 |
| KR | 20190011102 | A | 2/2019 |
| WO | WO 2016/167099 | A1 | 10/2016 |
| WO | WO2018029908 | A1 | 2/2018 |
| WO | WO 2019049506 | A1 | 3/2019 |
| WO | WO 2021/219811 | A1 | 11/2021 |

OTHER PUBLICATIONS

United States Office Action for corresponding U.S. Appl. No. 35/517,43, dated Apr. 23, 2024, 33 pages.
Japanese Office Action (w/ English Translation) for corresponding application JP2024515886, dated Jan. 21, 2025 , 8 pages.
PCT International Search Report and Written Opinion (with English translations) for corresponding PCT Application No. PCT/CN2022/136476, mailed Mar. 3, 2023, 13 pages.
Notice of Reasons for Refusal (with English translation) received in corresponding Application No. JP 2024515886, dated Jun. 10, 2025, 6 pages.
Extended European Search Report received in corresponding Application No. EP 22903359.2, dated Apr. 14, 2025, 9 pages.

* cited by examiner

ENDOSCOPIC BENDING SECTION AND ENDOSCOPE

CROSS-REFERENCE TO RELATED APPLICATIONS

This application is an U.S. national phase application under 35 U.S.C. § 371 based upon international patent application No. PCT/CN2022/136476, filed on Dec. 5, 2022, which itself claims priority to Chinese patent application No. 202111485757.0 filed on Dec. 7, 2021. The contents of the above identified applications are hereby incorporated herein in their entireties by reference.

TECHNICAL FIELD

The present disclosure relates to the technical field of medical devices, and in particular to an endoscopic bending section and an endoscope.

BACKGROUND

With the development of medical technology, endoscope technology has emerged. Endoscopes are configured to visually inspect hard-to-reach locations such as organs in the human body to observe pathological changes. Typically, the endoscope includes a long insertion tube having a handle at an end of the insertion tube adjacent to an operator, and a visual inspection device such as a built-in camera at a distal end of the long insertion tube. In order to be able to control the endoscope inside the human body, the endoscope includes a bendable bending section, and an orientation of a tip of an end of the bending section is adjusted through the bending of the bending section, thereby changing an observation angle.

According to the endoscope, the handle is connected to the bending section through two traction wires, thereby allowing the handle to control the bending section to bend in four directions. The traction wires and the bending section are connected in a welding mode. In the prior art, due to the high cost of endoscope, the endoscope is disinfected and cleaned after being used to achieve recycling. This method carries a risk of cross-infection due to incomplete disinfection. Therefore, disposable endoscopes have emerged, and the bending section and other components are made of plastic materials for one-time use.

However, it is currently difficult to connect the traction wires through welding to the disposable bending section. How to wrap the traction wires around the bending section without affecting the mounting of other components is an urgent problem to be solved.

SUMMARY

Accordingly, it is necessary to provide an endoscope bending section and an endoscope that can effectively be connected to traction wires, have strong stability, and do not affect the mounting of other components.

An endoscopic bending section includes: a connecting portion configured to be connected to a tip; and a winding portion connected to the connecting portion and provided with a mounting cavity, the winding portion being further provided with a first traction wire hole, a second traction wire hole, a third traction wire hole, and a fourth traction wire hole that are spaced apart around the mounting cavity. The mounting cavity, the first traction wire hole, the second traction wire hole, the third traction wire hole, and the fourth traction wire hole are arranged along an axial direction of the winding portion, the winding portion is provided with at least three wire passing holes, the at least three wire passing holes are spaced apart along a circumferential direction of the winding portion, and each wire passing hole is in communication with the mounting cavity. At least one wire passing hole is located between the first traction wire hole and the second traction wire hole, at least one wire passing hole is located between the second traction wire hole and the third traction wire hole, and at least one wire passing hole is located between the third traction wire hole and the fourth traction wire hole.

According to the endoscopic bending section, during a winding process, a traction wire extends from the bottom of the first traction wire hole along the axial direction of the winding portion from bottom to top, then extends through the winding portion through the wire passing hole between the first traction wire hole and the second traction wire hole, then extends into the winding portion through the wire passing hole between the second traction wire hole and the third traction wire hole, and finally extends from the top of the third traction wire hole along the axial direction of the winding portion from top to bottom. After that, another traction wire extends from the bottom of the second traction wire hole along the axial direction of the winding portion from bottom to top, then extends through the winding portion through the wire passing hole between the second traction wire hole and the third traction wire hole, then extends into the winding portion from the wire passing hole between the third traction wire hole and the fourth traction wire hole, and finally extends from the top of the fourth traction wire hole along the axial direction of the winding portion from top to bottom. The endoscopic bending section can stably connect two traction wires through the combination of four traction wire holes and at least three wire passing holes, so that the two traction wires can be effectively pulled in four directions, the wire winding is stable and is not easy to slip, and the traction wires do not occupy a position in the mounting cavity and does not affect the mounting of other components and the normal use of the endoscopic bending section.

In one of the embodiments, at least six wire passing holes are provided, the at least six wire passing holes include a first wire passing hole, a second wire passing hole, a third wire passing hole, a fourth wire passing hole, a fifth wire passing hole, and a sixth wire passing hole that are arranged sequentially along the circumferential direction of the winding portion, the first wire passing hole and the second wire passing hole are located between the first traction wire hole and the second traction wire hole, the third wire passing hole and the fourth wire passing hole are located between the second traction wire hole and the third traction wire hole, and the fifth wire passing hole and the sixth wire passing hole are located between the third traction wire hole and the fourth traction wire hole.

In one of the embodiments, the winding portion is further provided with a first guiding groove, the first guiding groove is provided on an outer wall of the winding portion, the first wire passing hole and the second wire passing hole are in communication with the first guiding groove, the winding portion is further provided with a second guiding groove, the second guiding groove is provided on the outer wall of the winding portion, the third wire passing hole and the fourth wire passing hole are in communication with the second guiding groove, the winding portion is further provided with a third guiding groove, the third guiding groove is provided on the outer wall of the winding portion, and the fifth wire passing hole and the sixth wire passing hole are in communication with the third guiding groove.

In one of the embodiments, the first guiding groove extends along the circumferential direction of the winding portion, the second guiding groove extends along the circumferential direction of the winding portion, and the third guiding groove extends along the circumferential direction of the winding portion.

In one of the embodiments, the winding portion is further provided with a mounting platform located on an inner wall of the mounting cavity, and the first traction wire hole, the second traction wire hole, the third traction wire hole, and the fourth traction wire hole are provided on the mounting platform.

In one of the embodiments, the mounting platform includes a first mounting platform, a second mounting platform, a third mounting platform, and a fourth mounting platform that are arranged sequentially along a circumferential direction of the mounting cavity, the first mounting platform is provided with the first traction wire hole, the second mounting platform is provided with the second traction wire hole, the third mounting platform is provided with the third traction wire hole, and the fourth mounting platform is provided with the fourth traction wire hole.

In one of the embodiments, the mounting platform is provided with a limiting portion configured to prevent a traction wire from entering the mounting cavity.

In one of the embodiments, the limiting portion includes a first boss corresponding to the first traction wire hole, a second boss corresponding to the second traction wire hole, a third boss corresponding to the third traction wire hole, and a fourth boss corresponding to the fourth traction wire hole, the first traction wire hole is located between the first boss and the inner wall of the mounting cavity, the second traction wire hole is located between the second boss and the inner wall of the mounting cavity, the third traction wire hole is located between the third boss and the inner wall of the mounting cavity, and the fourth traction wire hole is located between the fourth boss and the inner wall of the mounting cavity.

In one of the embodiments, the connecting portion and the winding portion are integrally formed by injection molding.

An endoscope includes the endoscopic bending section described in any one of the foregoing.

According to the endoscope, during a winding process, a traction wire extends from the bottom of the first traction wire hole along the axial direction of the winding portion from bottom to top, then extends through the winding portion through the wire passing hole between the first traction wire hole and the second traction wire hole, then extends into the winding portion through the wire passing hole between the second traction wire hole and the third traction wire hole, and finally extends from the top of the third traction wire hole along the axial direction of the winding portion from top to bottom. After that, another traction wire extends from the bottom of the second traction wire hole along the axial direction of the winding portion from bottom to top, then extends through the winding portion through the wire passing hole between the second traction wire hole and the third traction wire hole, then extends into the winding portion from the wire passing hole between the third traction wire hole and the fourth traction wire hole, and finally extends from the top of the fourth traction wire hole along the axial direction of the winding portion from top to bottom. The endoscopic bending section can stably connect two traction wires through the combination of four traction wire holes and at least three wire passing holes, so that the two traction wires can be effectively pulled in four directions, the wire winding is stable and is not easy to slip, and the traction wires do not occupy a position in the mounting cavity and does not affect the mounting of other components and the normal use of the endoscopic bending section.

BRIEF DESCRIPTION OF THE DRAWINGS

The drawings constitute a part of the present disclosure and are used to provide a further understanding of the present disclosure. The exemplary embodiments of the present disclosure and their descriptions are used to explain the present disclosure and do not constitute an improper limitation of the present disclosure.

In order to illustrate the embodiments of the present disclosure more clearly, the drawings used in the embodiments will be described briefly. Apparently, the following described drawings are merely for the embodiments of the present disclosure, and other drawings can be derived by those of ordinary skill in the art without any creative effort.

DESCRIPTION OF REFERENCE SIGNS

Figure 1:
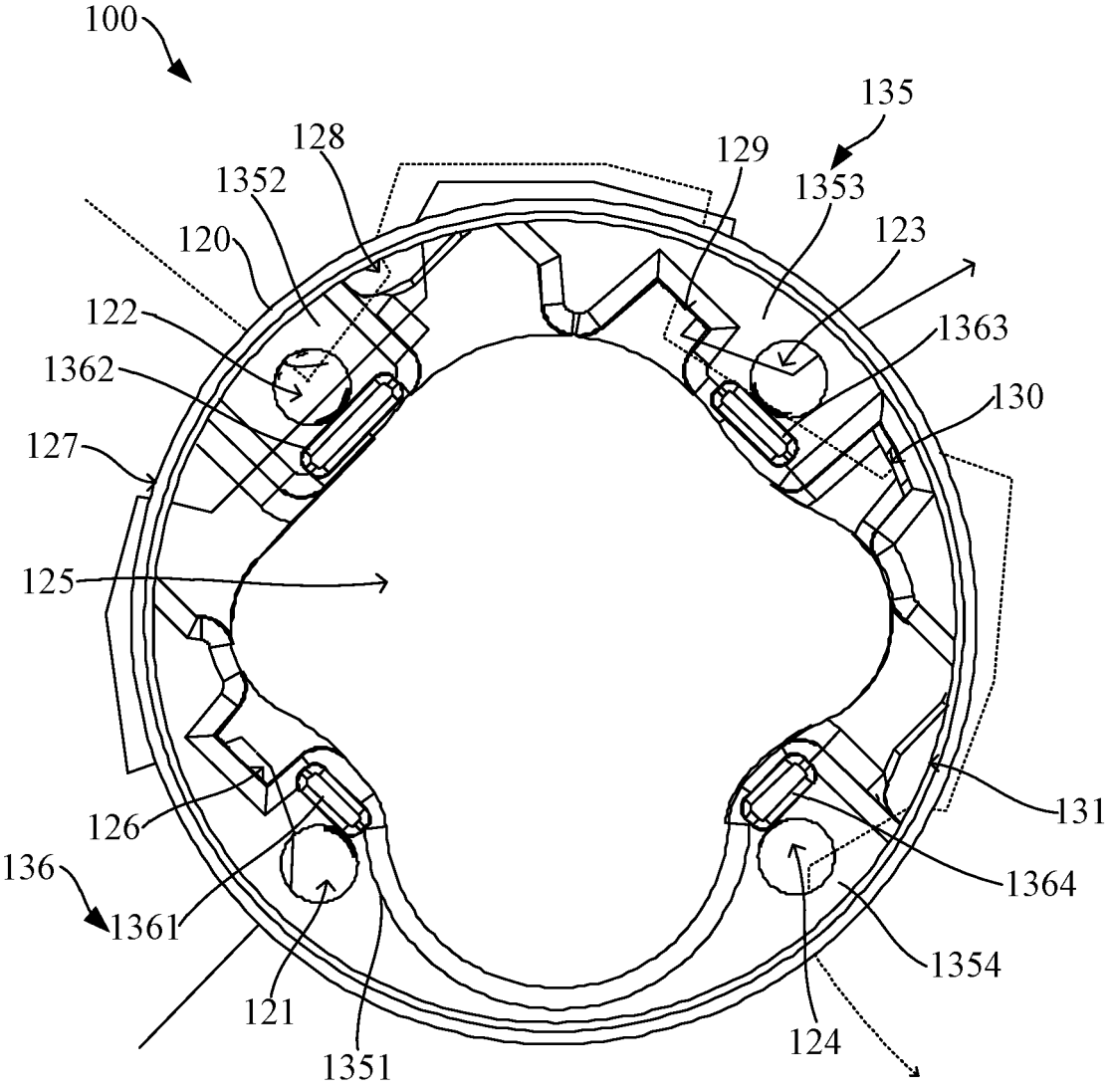
FIG. 1 is a first schematic view of an endoscopic bending section according to an embodiment.

100, endoscopic bending section; 110, connecting portion; 120, winding portion; 121, first traction wire hole; 122, second traction wire hole; 123, third traction wire hole; 124, fourth traction wire hole; 125, mounting cavity; 126, first wire passing hole; 127, second wire passing hole; 128, third wire passing hole; 129, fourth wire passing hole; 130, fifth wire passing hole; 131, sixth wire passing hole; 132, first guiding groove; 133, second guiding groove; 134, third guiding groove; 135, mounting platform; 1351, first mounting platform; 1352, second mounting platform; 1353, third mounting platform; 1354, fourth mounting platform; 136, limiting portion; 1361, first boss; 1362, second boss; 1363, third boss; 1364, fourth boss.

DETAILED DESCRIPTION OF THE EMBODIMENTS

In order to make the above objects, features and advantages of the present disclosure clear and easier to understand, the specific embodiments of the present disclosure are described in detail below in combination with the accompanying drawings. Many specific details are set forth in the following description to facilitate a full understanding of the present disclosure. However, the present disclosure can be implemented in many ways different from those described herein, and those skilled in the art can make similar improvements without departing from the connotation of the present disclosure. Therefore, the present disclosure is not limited by the specific embodiments disclosed below.

In the description of the present disclosure, it should be understood that the terms "center", "longitudinal", "transverse", "length", "width", "thickness", "upper", "lower", "front", "rear", "left", "right", "vertical", "horizontal", "top", "bottom", "inner", "outer", "clockwise", "counterclockwise", "axial", "radial", "circumferential direction" are based on the azimuth or position relationship shown in the attached drawings, which are only for the convenience of describing the present disclosure and simplifying the description, rather than indicating or implying that the device or element must have a specific azimuth, be constructed and operated in a specific azimuth, so such terms cannot be understood as a limitation of the present disclosure.

In addition, the terms "first" and "second" are only used for descriptive purposes and cannot be understood as indicating or implying relative importance or implicitly indicating the number of indicated technical features. Thus, the features defined with "first" and "second" may explicitly or implicitly include at least one of the features. In the description of the present disclosure, "a plurality of" means at least two, such as two, three, etc., unless otherwise expressly and specifically defined.

In the present disclosure, unless otherwise expressly specified and limited, the terms "mount", "connect", "contact", "fix" and other terms should be understood in a broad sense, for example, they can be fixed connections, detachable connections, or integrated. They can be mechanical connection or electrical connection. They can be directly connected or indirectly connected through an intermediate medium. They can be the connection within two elements or the interaction relationship between two elements, unless otherwise expressly limited. For those skilled in the art, the specific meaning of the above terms in the present disclosure can be understood according to the specific situation.

In the present disclosure, unless otherwise expressly specified and limited, the first feature "above" or "below" the second feature may be in direct contact with the first and second features, or the first and second features may be in indirect contact through an intermediate medium. Moreover, the first feature is "above" the second feature, but the first feature is directly above or diagonally above the second feature, or it only means that the horizontal height of the first feature is higher than the second feature. The first feature is "below" of the second feature, which can mean that the first feature is directly below or obliquely below the second feature, or simply that the horizontal height of the first feature is less than that of the second feature.

It should be noted that when an element is called "fixed to" or "provided on" another element, it can be directly on another element or there can be a centered element. When an element is considered to be "connected" to another element, it can be directly connected to another element or there may be intermediate elements at the same time. The terms "vertical", "horizontal", "up", "down", "left", "right" and similar expressions used herein are for the purpose of illustration only and do not represent the only embodiment.

In an embodiment, referring to FIGS. 1 to 4, an endoscopic bending section 100 includes a connecting portion 110 configured to be connected to a tip and a winding portion 120 connected to the connecting portion 110. The winding portion 120 is provided with a mounting cavity 125. The winding portion 120 is further provided with a first traction wire hole 121, a second traction wire hole 122, a third traction wire hole 123, and a fourth traction wire hole 124 that are spaced apart around the mounting cavity 125. The mounting cavity 125, the first traction wire hole 121, the second traction wire hole 122, the third traction wire hole 123, and the fourth traction wire hole 124 extend along an axial direction of the winding portion 120. The winding portion 120 is provided with at least three wire passing holes. The at least three wire passing holes are spaced apart along a circumferential direction of the winding portion 120. Each wire passing hole is in communication with the mounting cavity 125. At least one wire passing hole is located between the first traction wire hole 121 and the second traction wire hole 122, at least one wire passing hole is located between the second traction wire hole 122 and the third traction wire hole 123, and at least one wire passing hole is located between the third traction wire hole 123 and the fourth traction wire hole 124.

According to the endoscopic bending section 100, during a winding process, a traction wire extends from the bottom of the first traction wire hole 121 along the axial direction of the winding portion 120 from bottom to top, then extends through the winding portion 120 through the wire passing hole between the first traction wire hole 121 and the second traction wire hole 122, then extends into the winding portion 120 through the wire passing hole between the second traction wire hole 122 and the third traction wire hole 123, and finally extends from the top of the third traction wire hole 123 along the axial direction of the winding portion 120 from top to bottom. After that, another traction wire extends from the bottom of the second traction wire hole 122 along the axial direction of the winding portion 120 from bottom to top, then extends through the winding portion 120 through the wire passing hole between the second traction wire hole 122 and the third traction wire hole 123, then extends into the winding portion 120 from the wire passing hole between the third traction wire hole 123 and the fourth traction wire hole 124, and finally extends from the top of the fourth traction wire hole 124 along the axial direction of the winding portion 120 from top to bottom. The endoscopic bending section 100 can stably connect two traction wires through the combination of four traction wire holes and at least three wire passing holes, so that the two traction wires can be effectively pulled in four directions, the wire winding is stable and is not easy to slip, and the traction wires do not occupy a position in the mounting cavity 125 and does not affect the mounting of other components and the normal use of the endoscopic bending section 100.

In an embodiment, referring to FIG. 1, at least six wire passing holes are provided. The at least six wire passing holes include a first wire passing hole 126, a second wire passing hole 127, a third wire passing hole 128, a fourth wire passing hole 129, a fifth wire passing hole 130, and a sixth wire passing hole 131 that are arranged sequentially along the circumferential direction of the winding portion 120. The first wire passing hole 126 and the second wire passing hole 127 are located between the first traction wire hole 121 and the second traction wire hole 122. The third wire passing hole 128 and the fourth wire passing hole 129 are located between the second traction wire hole 122 and the third traction wire hole 123. The fifth wire passing hole 130 and the sixth wire passing hole 131 are located between the third traction wire hole 123 and the fourth traction wire hole 124. In this way, a new winding method is provided for the two traction wires. One of the traction wires extends through the first traction wire hole 121 from bottom to top, then extends through the winding portion 120 from the first wire passing hole 126, extends into the winding portion 120 through the second wire passing hole 127, extends through the winding portion 120 from the third wire passing hole 128, extends into the winding portion 120 through the fourth wire passing hole 129, and extends through the third traction wire hole 123 from top to bottom and is tightened to form a winding fixation. The other one of the traction wires extends through the second traction wire hole 122 from bottom to top, then extends through the winding portion 120 through the third wire passing hole 128, and extends into the winding portion 120 through the fourth wire passing hole 129, extends through the winding portion 120 from the fifth wire passing hole 130, extends into the winding portion 120 through the sixth wire passing hole 131, and extends through the fourth traction wire hole 124 from top to bottom and is tightened to form a winding fixation. Moreover, after tightening, the occupied space is further reduced, and the friction force is increased to avoid slipping, which is beneficial to improving the use quality and reliability of the endoscopic bending section 100. This embodiment only provides one specific winding method, but is not limited thereto.

Figure 2:
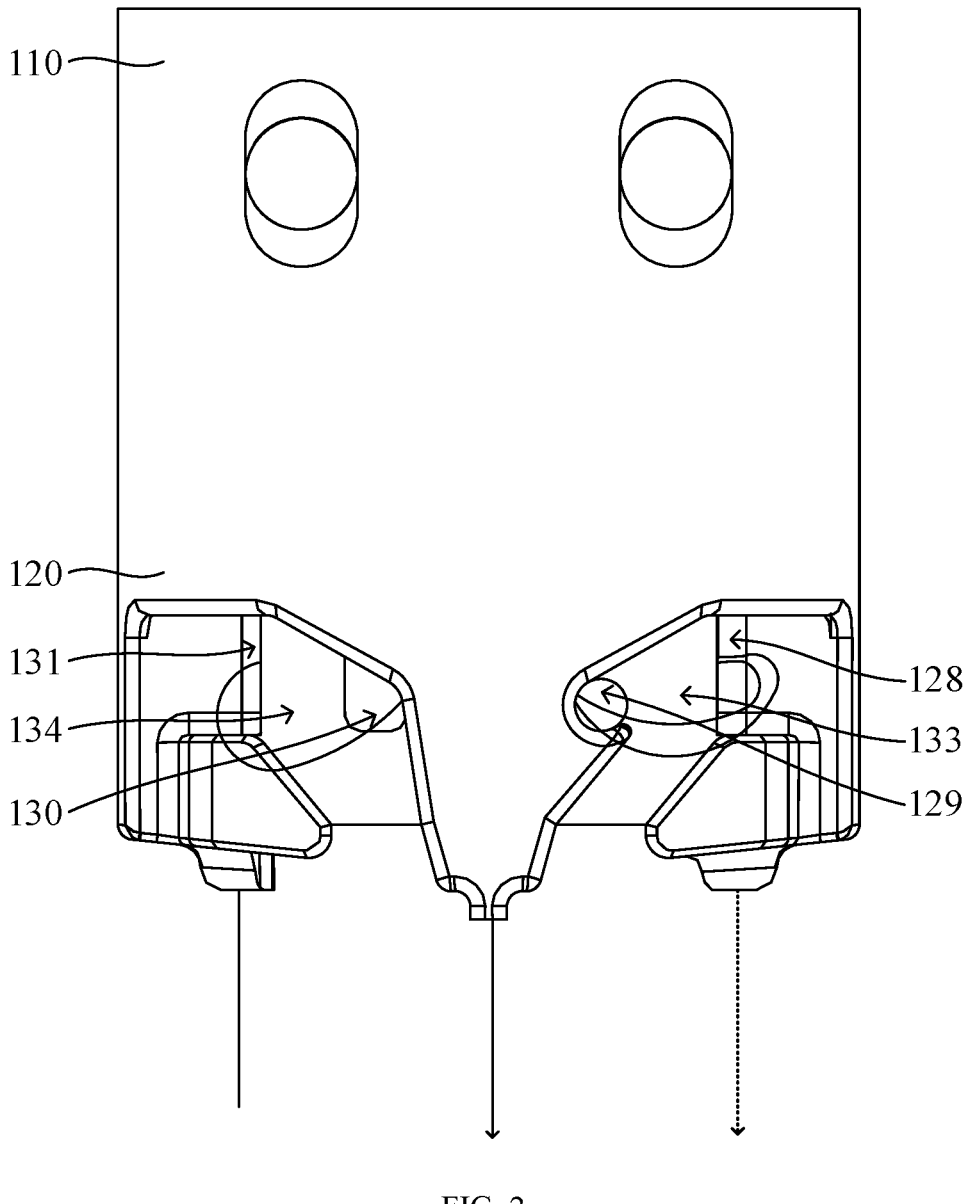
FIG. 2 is a second schematic view of an endoscopic bending section according to an embodiment.
Figure 3:
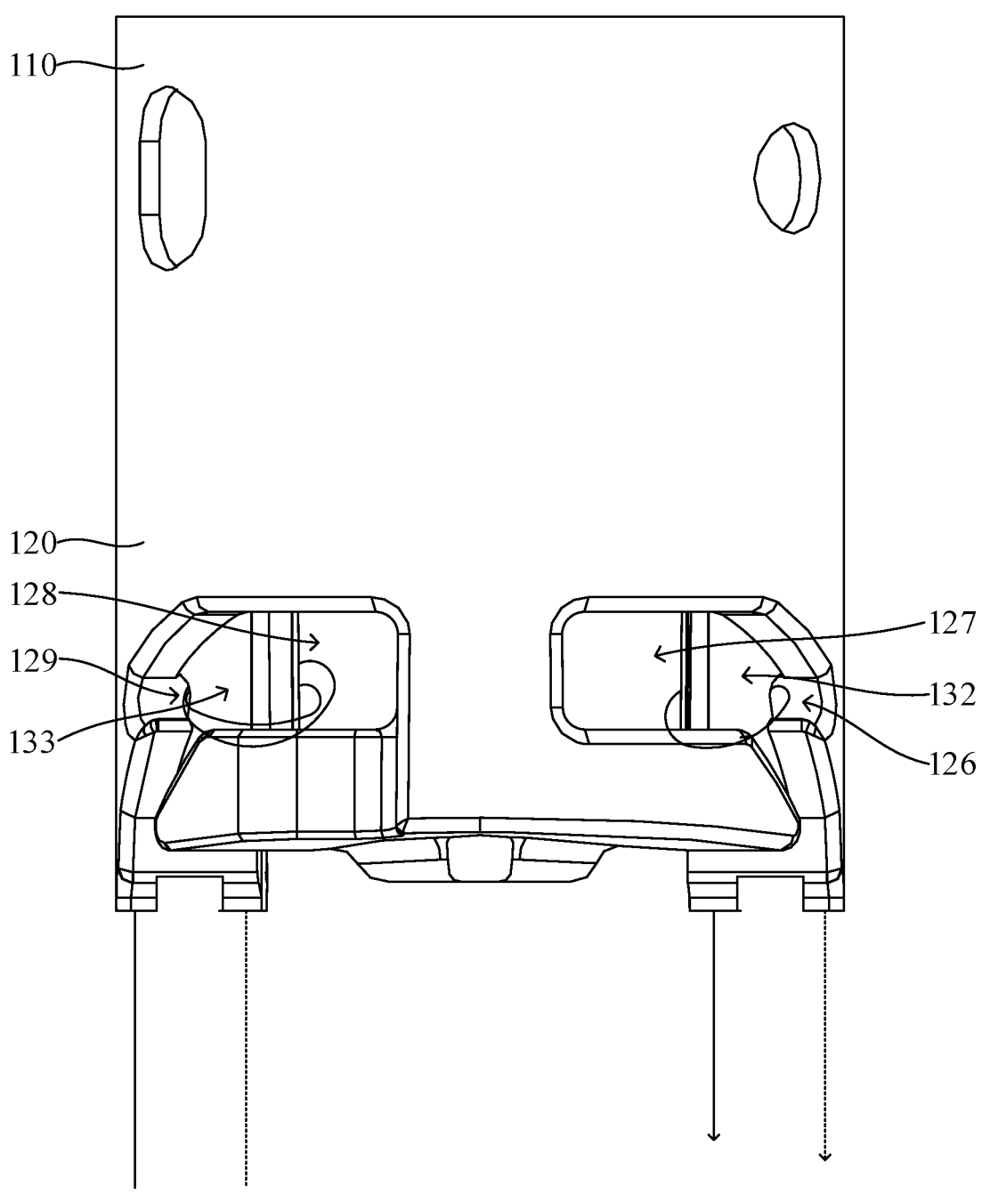
FIG. 3 is a third schematic view of an endoscopic bending section according to an embodiment.

In an embodiment, referring to FIGS. 1, 2 and 3, the winding portion 120 is further provided with a first guiding groove 132, and the first guiding groove 132 is provided on an outer wall of the winding portion 120. The first wire passing hole 126 and the second wire passing hole 127 are in communication with the first guiding groove 132. Furthermore, the winding portion 120 is further provided with a second guiding groove 133, and the second guiding groove 133 is provided on the outer wall of the winding portion 120. The third wire passing hole 128 and the fourth wire passing hole 129 are in communication with the second guiding groove 133. Furthermore, the winding portion 120 is further provided with a third guiding groove 134, and the third guiding groove 134 is provided on the outer wall of the winding portion 120. The fifth wire passing hole 130 and the sixth wire passing hole 131 are in communication with the third guiding groove 134. In this way, the traction wire can be hidden and can be prevented from protruding, the smoothness of the outer wall of the winding portion 120 can be ensured, and the probability of wear of the traction wire can be reduced.

Figure 4:
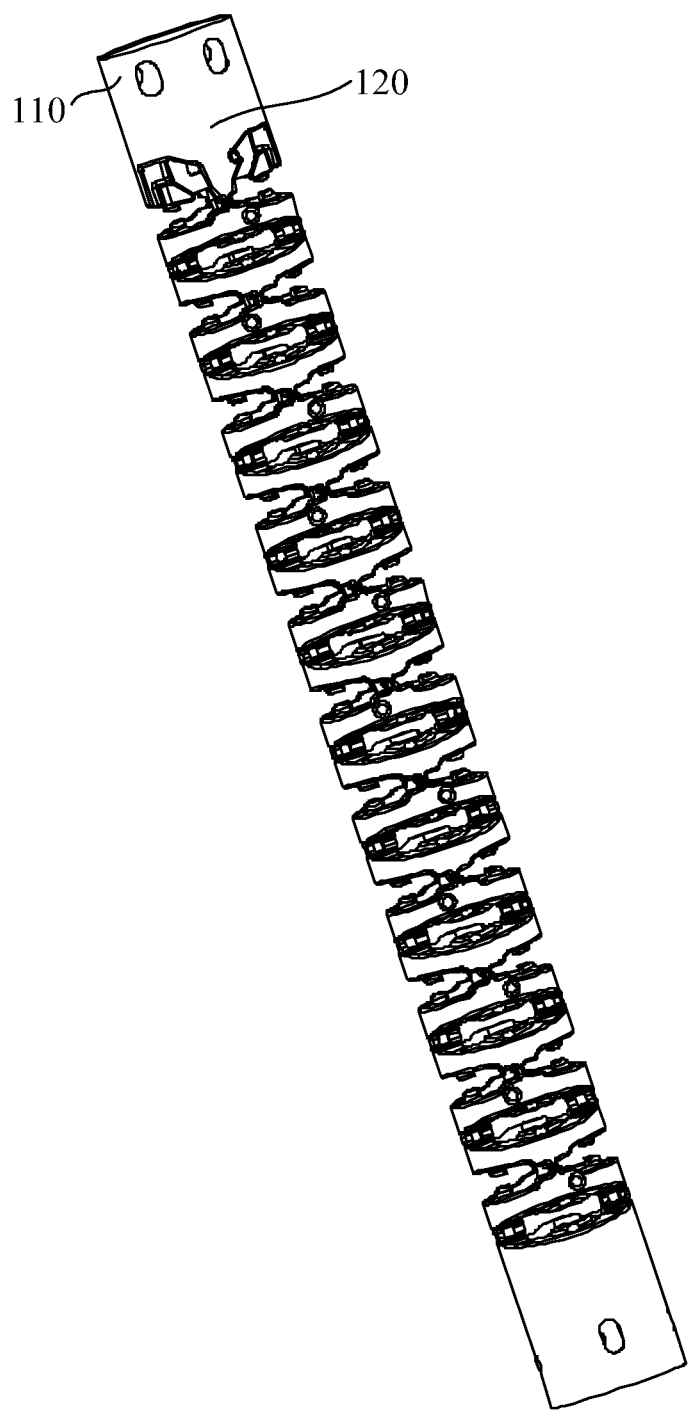
FIG. 4 is a schematic view of an overall structure of an endoscopic bending section according to an embodiment.

In an embodiment, referring to FIGS. 2, 3 and 4, the first guiding groove 132 extends along the circumferential direction of the winding portion 120. The second guiding groove 133 extends along the circumferential direction of the winding portion 120. The third guiding groove 134 extends along the circumferential direction of the winding portion 120. In this way, during the winding process, the guiding groove is beneficial to improve the convenience of winding.

In an embodiment, referring to FIG. 1, the winding portion 120 is further provided with a mounting platform 135. The mounting platform 135 is located on an inner wall of the mounting cavity 125, and the first traction wire hole 121, the second traction wire hole 122, the third traction wire hole 123, and the fourth traction wire hole 124 are provided on the mounting platform 135. In this way, a winding area can be limited to the mounting platform 135 without occupying a space of the mounting cavity 125, thereby avoiding affecting the mounting and use of other components.

In an embodiment, referring to FIG. 1, the mounting platform 135 includes a first mounting platform 1351, a second mounting platform 1352, a third mounting platform 1353, and a fourth mounting platform 1354 that are arranged sequentially along a circumferential direction of the mounting cavity 125. The first mounting platform 1351 is provided with the first traction wire hole 121, the second mounting platform 1352 is provided with the second traction wire hole 122, the third mounting platform 1353 is provided with the third traction wire hole 123, the fourth mounting platform 1354 is provided with the fourth traction wire hole 124. In this way, opening positions are provided for the first traction wire hole 121, the second traction wire hole 122, the third traction wire hole 123, and the fourth traction wire hole 124, respectively, and it is beneficial to enhance the structural strength of the winding portion 120.

In an embodiment, referring to FIG. 1, the mounting platform 135 is provided with a limiting portion 136 configured to prevent the traction wire from entering the mounting cavity 125. In this way, the traction wire can be limited on the mounting platform 135 through the limiting portion 136 without occupying the space of the mounting cavity 125, thereby avoiding affecting the mounting and use of other components.

Specifically, referring to FIG. 1, the limiting portion 136 includes a first boss 1361 corresponding to the first traction wire hole 121, a second boss 1362 corresponding to the second traction wire hole 122, a third boss 1363 corresponding to the third traction wire hole 123, and a fourth boss 1364 corresponding to the fourth traction wire hole 124. The first traction wire hole 121 is located between the first boss 1361 and the inner wall of the mounting cavity 125. The second traction wire hole 122 is located between the second boss 1362 and the inner wall of the mounting cavity 125. The third traction wire hole 123 is located between the third boss 1363 and the inner wall of the mounting cavity 125. The fourth traction wire hole 124 is located between the fourth boss 1364 and the inner wall of the mounting cavity 125. In this way, through the limiting effects of the first boss 1361, the second boss 1362, the third boss 1363 and the fourth boss 1364, the traction wire can be further limited on the mounting platform 135.

Optionally, the connection method of the connecting portion 110 and the winding portion 120 may be inserting, riveting, bonding, snap connection or other connection methods. Alternatively, the connecting portion 110 and the winding portion 120 are integrally formed.

Specifically, referring to FIGS. 1, 2, 3 and 4, the connecting portion 110 and the winding portion 120 are integrally formed by injection molding. In this way, the structure is simple, easy to manufacture, and low in cost. At the same time, it is helpful to improve the connection stability of the connecting portion 110 and the winding portion 120, thereby ensuring the structural stability of the endoscopic bending section 100. This embodiment only provides one specific connection method between the connecting portion 110 and the winding portion 120, but is not limited thereto.

In an embodiment, an endoscope (not shown) includes the endoscopic bending section 100 of the above embodiment.

According to the endoscope, during a winding process, a traction wire extends from the bottom of the first traction wire hole 121 along the axial direction of the winding portion 120 from bottom to top, then extends through the winding portion 120 through the wire passing hole between the first traction wire hole 121 and the second traction wire hole 122, then extends into the winding portion 120 through the wire passing hole between the second traction wire hole 122 and the third traction wire hole 123, and finally extends from the top of the third traction wire hole 123 along the axial direction of the winding portion 120 from top to bottom. After that, another traction wire extends from the bottom of the second traction wire hole 122 along the axial direction of the winding portion 120 from bottom to top, then extends through the winding portion 120 through the wire passing hole between the second traction wire hole 122 and the third traction wire hole 123, then extends into the winding portion 120 from the wire passing hole between the third traction wire hole 123 and the fourth traction wire hole 124, and finally extends from the top of the fourth traction wire hole 124 along the axial direction of the winding portion 120 from top to bottom. The endoscopic bending section 100 can stably connect two traction wires through the combination of four traction wire holes and at least three wire passing holes, so that the two traction wires can be effectively pulled in four directions, the wire winding is stable and is not easy to slip, and the traction wires do not occupy a position in the mounting cavity 125 and does not affect the mounting of other components and the normal use of the endoscopic bending section 100.

The above-mentioned embodiments do not constitute a limitation on the protection scope of the technical solution. Any modifications, equivalent replacements and improvements made within the spirit and principles of the above-mentioned embodiments shall be included within the protection scope of this technical solution.

The foregoing descriptions are merely specific embodiments of the present disclosure, but are not intended to limit the protection scope of the present disclosure. Any variation or replacement readily figured out by a person skilled in the art within the technical scope disclosed in the present disclosure shall all fall within the protection scope of the present disclosure.

What is claimed is:

1. An endoscopic bending section comprising:
a connecting portion configured to be connected to a tip; and
a winding portion connected to the connecting portion and provided with a mounting cavity, the winding portion being further provided with a first traction wire hole, a second traction wire hole, a third traction wire hole, and a fourth traction wire hole that are spaced apart around the mounting cavity, wherein the mounting cavity, the first traction wire hole, the second traction wire hole, the third traction wire hole, and the fourth traction wire hole are arranged extending along an axial direction of the winding portion, the winding portion is provided with at least three wire passing holes spaced apart along a circumferential direction of the winding portion, and each wire passing hole is in communication with the mounting cavity;
wherein at least one wire passing hole is located between the first traction wire hole and the second traction wire hole, at least one wire passing hole is located between the second traction wire hole and the third traction wire hole, and at least one wire passing hole is located between the third traction wire hole and the fourth traction wire hole;
wherein at least six wire passing holes are provided, the at least six wire passing holes comprise a first wire passing hole, a second wire passing hole, a third wire passing hole, a fourth wire passing hole, a fifth wire passing hole, and a sixth wire passing hole that are arranged sequentially along the circumferential direction of the winding portion, the first wire passing hole and the second wire passing hole are located between the first traction wire hole and the second traction wire hole, the third wire passing hole and the fourth wire passing hole are located between the second traction wire hole and the third traction wire hole, and the fifth wire passing hole and the sixth wire passing hole are located between the third traction wire hole and the fourth traction wire hole.

2. The endoscopic bending section according to claim 1, wherein the winding portion is further provided with a first guiding groove, the first guiding groove is provided on an outer wall of the winding portion, the first wire passing hole and the second wire passing hole are in communication with the first guiding groove,
wherein the winding portion is further provided with a second guiding groove, the second guiding groove is provided on the outer wall of the winding portion, the third wire passing hole and the fourth wire passing hole are in communication with the second guiding groove,
wherein the winding portion is further provided with a third guiding groove, the third guiding groove is provided on the outer wall of the winding portion, and the fifth wire passing hole and the sixth wire passing hole are in communication with the third guiding groove.

3. The endoscopic bending section according to claim 2, wherein the first guiding groove extends along the circumferential direction of the winding portion, the second guiding groove extends along the circumferential direction of the winding portion, and the third guiding groove extends along the circumferential direction of the winding portion.

4. The endoscopic bending section according to claim 1, wherein the winding portion is further provided with a mounting platform located on an inner wall of the mounting cavity, and the first traction wire hole, the second traction wire hole, the third traction wire hole, and the fourth traction wire hole are provided on the mounting platform.

5. The endoscopic bending section according to claim 4, wherein the mounting platform comprises a first mounting platform, a second mounting platform, a third mounting platform, and a fourth mounting platform that are arranged sequentially along a circumferential direction of the mounting cavity, the first mounting platform is provided with the first traction wire hole, the second mounting platform is provided with the second traction wire hole, the third mounting platform is provided with the third traction wire hole, and the fourth mounting platform is provided with the fourth traction wire hole.

6. The endoscopic bending section according to claim 4, wherein the mounting platform is provided with a limiting portion configured to prevent a traction wire from entering the mounting cavity.

7. The endoscopic bending section according to claim 6, wherein the limiting portion comprises a first boss corresponding to the first traction wire hole, a second boss corresponding to the second traction wire hole, a third boss corresponding to the third traction wire hole, and a fourth boss corresponding to the fourth traction wire hole, the first traction wire hole is located between the first boss and the inner wall of the mounting cavity, the second traction wire hole is located between the second boss and the inner wall of the mounting cavity, the third traction wire hole is located between the third boss and the inner wall of the mounting cavity, and the fourth traction wire hole is located between the fourth boss and the inner wall of the mounting cavity.

8. The endoscopic bending section according to claim 1, wherein the connecting portion and the winding portion are integrally formed by injection molding.

9. An endoscope comprising the endoscopic bending section according to claim 1.

* * * * *